United States Patent
Stifter et al.

(10) Patent No.: US 11,510,738 B2
(45) Date of Patent: Nov. 29, 2022

(54) SURGICAL INSTRUMENT SYSTEM

(71) Applicant: MEDIVATION AG, Brugg (CH)

(72) Inventors: Jan Stifter, Schneisingen (CH); Tobias Schwägli, Solothurn (CH)

(73) Assignee: MEDIVATION AG, Brugg (CH)

( * ) Notice: Subject to any disclaimer, the term of this patent is extended or adjusted under 35 U.S.C. 154(b) by 194 days.

(21) Appl. No.: 16/610,462

(22) PCT Filed: Apr. 26, 2018

(86) PCT No.: PCT/EP2018/060693
§ 371 (c)(1),
(2) Date: Nov. 1, 2019

(87) PCT Pub. No.: WO2018/202529
PCT Pub. Date: Nov. 8, 2018

(65) Prior Publication Data
US 2021/0153948 A1 May 27, 2021

(30) Foreign Application Priority Data
May 2, 2017 (CH) .................................... 00585/17

(51) Int. Cl.
*A61B 34/20* (2016.01)
*A61B 90/00* (2016.01)

(52) U.S. Cl.
CPC .............. *A61B 34/20* (2016.02); *A61B 90/37* (2016.02); *A61B 2034/2048* (2016.02);
(Continued)

(58) Field of Classification Search
CPC ........ A61B 2034/102; A61B 2034/105; A61B 2034/2048; A61B 2034/2055;
(Continued)

(56) References Cited

U.S. PATENT DOCUMENTS 8,608,748 B2 12/2013 Metzger et al.
8,641,721 B2 2/2014 Aram et al.
(Continued)

FOREIGN PATENT DOCUMENTS

WO 9325157 A1 12/1993
WO 2012007561 A2 1/2012
(Continued)

OTHER PUBLICATIONS

Stojanov et al., "Preliminary Investigation of Evaluating Surgical Performance Using an IMU Device," 2012, IEEE World Congress on Computational Intelligence, pp. 1-8 (Year: 2012).*
(Continued)

*Primary Examiner* — Joseph M Santos Rodriguez
*Assistant Examiner* — Maria Christina Talty
(74) *Attorney, Agent, or Firm* — Hard IP LLC

(57) ABSTRACT

A surgical instrument system for treatment of an anatomical structure comprises an instrument and/or a patient specific instrument. The instrument and/or the patient specific instrument comprises an integrated measurement system for tracking the instrument and/or the patient specific instrument relative to the anatomical structure. The integrated measurement system comprises a tracking system, which comprises a shadow imaging tracking system comprising an optical source, a shadow-generating device and a patient specific instrument sensor. An initial position of the instrument or the patient specific instrument is registerable by the patient specific instrument sensor. The shadow-generating device is arranged between the optical source and the imaging device for generating a shadow. The shadow imaging tracking system is configured to compute the elevation of the source from the pattern the shadow casts on the surface of the imaging device. The integrated measurement system com-
(Continued)

prises an inertial measurement unit to determine the patient's position.

20 Claims, 3 Drawing Sheets

(52) U.S. Cl.
CPC .............. *A61B 2034/2055* (2016.02); *A61B 2034/2065* (2016.02); *A61B 2090/373* (2016.02); *A61B 2560/0214* (2013.01)

(58) Field of Classification Search
CPC ...... A61B 2034/2065; A61B 2090/373; A61B 2560/0214; A61B 34/20; A61B 90/37; G01D 5/34

See application file for complete search history.

(56) References Cited

U.S. PATENT DOCUMENTS

| 8,911,447 | B2* | 12/2014 | van der Walt | A61B 34/20 606/102 |
| 2008/0319491 | A1* | 12/2008 | Schoenefeld | A61B 90/37 606/86 R |
| 2009/0088763 | A1 | 4/2009 | Aram et al. | |
| 2012/0239045 | A1 | 9/2012 | Li | |
| 2013/0261633 | A1* | 10/2013 | Thornberry | A61F 2/4609 606/91 |
| 2013/0274633 | A1* | 10/2013 | Hladio | A61B 5/1072 600/587 |
| 2014/0066720 | A1 | 3/2014 | Wilkinson et al. | |
| 2016/0209248 | A1* | 7/2016 | Hasler | G01S 5/16 |
| 2016/0228204 | A1* | 8/2016 | Quaid | A61B 17/1703 |
| 2016/0256155 | A1* | 9/2016 | Shelton, IV | A61B 17/068 |
| 2018/0168759 | A1* | 6/2018 | Kilroy | B25J 13/025 |

FOREIGN PATENT DOCUMENTS

| WO | 2013152436 A1 | 10/2013 | |
| WO | WO-2016139638 A1 * | 9/2016 | ............ A61B 34/30 |
| WO | 2016139638 A1 | 9/2019 | |

OTHER PUBLICATIONS

International Application No. PCT/EP2018/060693, International Search Report dated Sep. 18, 2018, 4 pages.
Chebira et al., "Nanotracking for Image-guided Microsurgery Hear-Restore RTD", 2013, www.nano-tera.ch/pdf/posters2014/HearRestore541.pdf, 1 page.
Edo Franzi, "Vision Embedded Systems—CSEM, SpaceCoder Technology", 2013, www.swissmntnetwork.ch/content/wp-content/uploads/2013/06/SpaceCoder1.pdf, pp. 1-32.
Hearrestore RTD et al., "First HearRestore Demonstrator!? Consists of a Camera Accracy Studies for Nanotracking in Image-Guided Microsurgery Accuracy Studies Demonstrator and Tracking Accuracy", www.nano-tera.ch/pdf/posters2015/HearRestore381.pdf, 1 page.
International Application No. PCT/EP2018/060693, Written Opinion of the International Searching Authority, dated Sep. 18, 2018, 9 pages.

* cited by examiner

SURGICAL INSTRUMENT SYSTEM

CROSS-REFERENCE TO RELATED APPLICATIONS

This application is a U.S. national stage filing under 35 U.S.C. 371 of international patent application no. PCT/EP2018/060693, filed on Apr. 26, 2018, which claims priority to Swiss patent application no. CH00585/17, filed on May 2, 2017, the contents of both of which are incorporated herein by reference in their entirety.

TECHNICAL FIELD

The invention is related to a surgical instrument system comprising an instrument and/or a patient specific instrument that incorporates measurement functionality to enable and to improve computer assisted surgical navigation. Thereby, a combination of the advantages of the instrument or the patient specific instrument with computer-assisted surgery is possible in particular for determining the position of a patient with respect to the instrument and/or the patient specific instrument more accurately.

Under patient specific instruments, it is to be understood mechanical instrumentation, such as templates manufactured according to the results of pre-operative or post-operative scans of an anatomic structure of a patient, which requires a surgical treatment which are adapted to the specific characteristics of the anatomic structure of the patient.

DESCRIPTION OF RELATED ART

A patient specific instrument is to be understood as a template which is mounted on an anatomical structure of a patient, which can serve as a reference guide for measuring or treating the bone, e.g. for positioning an implant or preparing a portion of a bone for an implant by performing a working step. An individual template has been described in the patent application WO9325157A1, which copies completely or by segments the surface of the osseous structure from CT images, from which the three-dimensional shape of the surface of the osseous structure is obtained. The template serves during operation as a reference guide for performing any working step, such as cutting, drilling, boring or milling of the osseous structure. Thereby each working step can be performed accurately by using the template as a precise dimensional reference guide. Thereby the time-consuming measuring and aligning work is shifted into the pre-operative phase, which allows for a simplification and acceleration of the intraoperative phase, reducing the duration of the intraoperative phase for the patient.

The patient specific instrument is referred to also as the patient matched device in the literature. In particular, the patient specific instrument can be the patient specific cut guide in total knee replacement. Prior to manufacturing a patient specific cut guide, a patient undergoes a CT or MRI scan from which accurate three-dimensional models of the bones are obtained. A pre-operative planning is performed with these three-dimensional models and the patient specific cut guide model is designed by a computer aided design program. The patient specific cut guide model is manufactured by a stereolithographic or an additive manufacturing method. One of the advantages of using a patient specific cut guide is the reduction of required operation time as the surgeon can execute the pre-operative plan very efficiently. A drawback of the patient specific cut guide is that additional time is required to check and approve the pre-operative plan. Moreover, no change to the plan is possible during surgery. Consequently, an implant position cannot be individually adapted during surgery to ensure a stable and well-functioning knee joint especially regarding proper balanced ligaments.

It is also possible to use a patient specific guide element in combination with a surgical navigation system and/or robotics for registration the patient's anatomy. Instead of registering the anatomy by palpation of landmarks and surface areas, the patient-specific instruments allow a simple and direct registration of the anatomy with preoperative image data. The term "registration" as well as the term "register" refer to the act of determining a relative position between an object, such as a bone or an instrument and a respective sensor unit.

In the patent documents US20090088763 A1, US 20140066720, U.S. Pat. No. 8,608,748, US20120239045, U.S. Pat. No. 8,641,721 B2 different types and applications for patient specific instruments are disclosed, especially in the field of total knee replacement or total ankle replacement (see e.g. US20120239045). They differ by the type of application and the way they mate with the corresponding bone structures.

A patient specific instrument is therefore used to register the patient's anatomy directly and provides the flexibility of computer-assisted surgery to allow the surgeon to adjust and fine-tune the implant position during surgery as well as to ensure proper ligament balancing. A computer assisted surgical system allows measuring or registering the patient's anatomy using markers attached to the patient's bone that are tracked by stereo camera system. One of the main applications of computer-assisted surgical systems is the total knee replacement, which is one of the most widely performed or orthopedic procedures worldwide. However, currently only 5 to 10% of the total knee replacements are performed by using a computer assisted surgical system. Amongst the reasons for this low percentage are to be named: additional costs for the navigated procedures, in particular the purchase cost of a system and the costs of the trackers and its cost of sterilization and increased operation time due to the more complex workflow and registration of landmarks and additional incisions or pins to mount the trackers.

The combination of patient specific instruments with a surgical navigation system for referencing the bone position is described in US2008319491 A1. According to the teaching of document, US2008319491 A1 there is disclosed a method of directly registering the patient's anatomy for surgical navigation procedures using patient matched instruments carrying a reference marker.

Mobile instrument integrated tracking systems for surgical navigation are described in US2008319491 A1 and US 20130274633 A1, in particular the concept of miniaturized and mobile tracking system and their applications in surgical procedures. There is no disclosure of any combination of such an integrated measurement system with a patient specific instrumentation.

A combination of patient specific instrumentation with mobile tracking technology is described in US 20130274633 A1 and WO2013152436 A1. These documents describe a combination of patient specific instrumentation with surgical navigation, in that the tracked instrument has a reference marker integrated into the patient specific instrument. A method to align the measurement system with the patient's anatomy by using a patient specific instrument is also disclosed. However, there is no disclosure of integrating the measurement system directly with the patient specific instrument.

There is a need to provide a patient specific instrument mounted on an anatomical structure, which can be tracked to allow for computer assisted surgical care of the anatomic structure, whereby a surgical tool can be operated remotely or with remote assistance. In particular, there is a need of a computer assisted navigation system for a surgical tool, if the surgical site is difficult to access or it is difficult to obtain an accurate picture of the position of the patient's anatomic structure. In particular, if treatment of a joint is required, it will be required that the position of a plurality of engaging or interacting anatomical structures is aligned. Moreover, a treatment of a joint may require a kinematic analysis of the movement of the members making up the joint.

The problem to be solved by the invention is to provide a more accurate position measuring system and tracking system for an instrument or a patient specific instrument. In particular, it is an object of the invention to determine the position of the patient more accurately.

The problem is solved by integrating the measurement system directly with the instrument or the patient specific instrument. Thereby a more accurate position information of the patient specific instrument can be obtained. Moreover, the positioning information of the patient specific instrument can be related to the position of an instrument, such as a surgical tool, relative to the patient specific instrument. Thereby the instrument can be guided accurately to provide the treatment of the anatomical structure as the treatment procedure can be visualized so to enable the operating personnel to perform a precise treatment of the anatomic structure. Moreover, the visualization can be compared on site with the patient's situation and any mismatch can be corrected.

The problem is thus solved by the subject matter as claimed in claim 1. Further advantageous embodiments are subject to the dependent claims.

SUMMARY OF THE INVENTION

A surgical instrument system for treatment of an anatomical structure comprises an instrument and/or a patient specific instrument for performing the treatment of the anatomical structure and an instrument, such as for instance a surgical tool. In particular, the instrument or the patient specific instrument can be attached to the anatomical structure. The instrument or the patient specific instrument comprises an integrated measurement system for tracking the instrument or the patient specific instrument relatively to the anatomical structure. The tracking system comprises a shadow imaging tracking system comprising an optical source, a shadow-generating device and a patient specific instrument sensor. The patient specific instrument can be a template for allowing the operating personnel to perform an exact treatment of the anatomical structure such as a cut of a bone structure, the positioning of an implant or a fixation means.

Under the term integrated measurement system, it is intended that the measurement system can be attached to instrument or the patient specific instrument. Under these conditions, the position of the instrument or the patient specific instrument is fixed relative to the measurement system. If the measurement system can be tracked by a tracking system, e.g. by directing a light beam onto its surface, the position of the measurement system is automatically defined. The integrated measurement system comprises a shadow imaging tracking system. The shadow imaging tracking system comprises an optical source, a shadow generating device, an imaging device and a patient specific instrument sensor. An initial position of the instrument or the patient specific instrument is registerable by the patient specific instrument sensor. The shadow-generating device is arranged between the optical source and the imaging device for generating a shadow. The shadow imaging tracking system is configured to compute the elevation of the optical source from the pattern the shadow casts on the surface of the imaging device. The integrated measurement system comprises an inertial measurement unit configured to determine the position of the patient. The position of the patient can be determined by means of a positioning sensor.

In other words, the surgical instrument system comprises an instrument or a patient specific instrument attached to an anatomical structure for performing a surgery on the anatomical structure. An initial position of the instrument or the patient specific instrument can be registered by one or a plurality of patient specific instrument sensors, such that an instrument position or a patient specific instrument position information and a precise patient position information is obtainable which is transformable into an instrument coordinate position information or a patient specific instrument coordinate position information and a patient position coordinate information in a three dimensional coordinate system by a computer. The position of the instrument sensor or the one or the plurality of patient specific instrument sensors thus matches with the position of the respective instrument or the patient specific instrument. Furthermore, an initial position information of the instrument or the patient specific instrument and the patient's position is obtainable by providing a signal-emitting element on the instrument or the patient specific instrument. Thereby an instrument position information or a patient specific instrument position information is obtainable which is transformable into an instrument position coordinate information or a patient specific instrument position coordinate and a patient position coordinate information in a three dimensional coordinate system by the computer, such that the patient specific instrument coordinate position information can be matched with the instrument coordinate position information or the instrument coordinate position information can be matched with another instrument coordinate position information or the patient specific instrument coordinate position information can be matched with another patient specific instrument coordinate position information. The patient specific instrument or the instrument comprises an integrated measurement system for tracking the instrument relative to the anatomical structure and an inertial measurement unit configured to determine the position of the patient. The position of the patient specific instrument or the instrument in relation to one of another instrument or a patient specific instrument can be displayed on a screen, which receives the imaging data from the computer to visualize the patient's anatomical structure, the patient specific instrument or the instrument attached to the anatomical structure and the instrument or the other patient specific instrument for determining the position of the patient. Thereby the surgical treatment to be performed by means of the instrument can be tracked and visualized in real-time and can be related precisely to a specific patient's position. Thereby, the integrated measurement system comprises a tracking system. The tracking system comprises a shadow imaging tracking system. The instrument can be one of a surgical tool or guide. A tracker element can be fixed to the anatomical structure. Such an anatomical structure can comprise a bone of a patient. The instrument is disposed with an attached or integrated shadow imaging measuring system. The shadow imaging tracking system comprises the tracker element and the attached or integrated shadow imaging measuring system. Therewith, the instrument can be navigated directly to the anatomical structure. The anatomical structure can be registered by means of landmarks or surface areas, which are registered by means of a pointing instrument disposed with a measuring system. This application is preferred if the position of instruments relative to each other or to an anatomical structure are to be measured in a limited working space, such as an OP field. In addition, the inertial measurement unit of the integrated measurement system is configured to determine the position of the patient.

Due to the fact, that the shadow imaging tracking system comprises a tracker element and a shadow imaging measuring system, in particular a shadow imaging sensor, of small size, an integration of the entire shadow imaging tracking system into a grip element of an instrument or a casing of the instrument is possible.

The shadow imaging tracking system can communicate with other instruments and/or a display. Thus, the measurement data can be displayed directly on an integrated display or can be transmitted to a processing unit in particular by wireless transmission. The processing unit can process the measurement data and shows the measurement data on a display. Such a display can be part of a tablet or other mobile device with integrated display. Each instrument can be disposed with its own display for the display of particular results or parameters, which may be provided from centrally e.g. from the processing unit or may be generated on the spot, e.g. by a local processing unit integrated into the instrument.

In case of the presence of multiple sensors, the measurement values of any of these sensors can be exchanged with each other or can be transmitted to the central processing unit. Any of the sensors can be disposed with its own processing unit or display.

According to an embodiment, the measurement system is configured to comprise an instrument comprising a tracker element, including multiple light sources such as LEDS (Light emitting diodes) and an imaging sensor. Thereby measurement redundancy is obtainable. In particular, two or more tracker elements can measure each other, thereby the precision and reliability of the measurement can be increased.

According to an embodiment, the shadow imaging tracking system can comprise a plurality of tracker elements or sensors comprising LED in a different orientation. By using a plurality of tracker elements or sensors, which are arranged in a different orientation to each other, a larger measurement space can be covered.

According to an embodiment, the position of an instrument can be determined indirectly by a second or further tracker element or sensor.

According to an embodiment, a position measurement of a first anatomical structure and a second anatomical structure is performed, whereby the first anatomical structure is disposed with a first patient specific instrument and the second anatomical structure is disposed with a second patient specific instrument, whereby the second instrument is fixed to the second anatomical structure to track the position of this structure relative to the first anatomical structure. In particular, the second instrument can also a patient specific instrument mating to a portion of a second anatomical structure. Alternatively, or in addition thereto, the second instrument is a portion of a secondary system which also incorporates a tracking system allowing redundant measurements. Any of the position measurements of the first or second anatomical structure can be combined with the measurement of the patient's position as obtained by the inertial measurement unit.

The use of a patient specific instrument comprising for instance a patient specific cutting body element has the advantage, that the configuration of the anatomical structure may be registered by the patient specific instrument. By making use of a patient specific instrument, time can be saved and the procedure for orienting the instrument can be simplified, whereby a number of sources for possible errors can be reduced.

According to an embodiment, at least one of a patient specific instrument or an instrument is tracked relative to the anatomical structure. In particular, multiple patient specific instruments or multiple instruments can be tracked relative to the anatomical structure. In particular, at least one of the patient specific instruments or instruments is equipped with the tracking system that allows any combination of relative measurement between the patient specific instruments and/or instruments.

According to an embodiment, the tracking system can be attached to multiple instruments.

According to an embodiment, the patient specific instrument and the tracked instrument, in particular the tracked surgical tool, and the inertial measurement unit are formed as a single unit and there are means to adjust position and/or rotation of the tracked instruments relative to the patient specific instrument. An adjustment can be restricted to a single or multiple movement, whereby the movement can be one of a linear movement or a rotational movement, or the movement is restricted by means of a mechanical interface.

According to an embodiment, the tracking system is one of an optical tracking system, a passive tracking system an active tracking system or a shadow imaging tracking system. In particular, the tracking system is an optical tracking system with a single or a plurality of optical sensors. The shadow imaging tracking system can track the 6D position of the tracker with three or more light sources, such as LEDs is tracked by measuring the shadow image on an optical sensor.

The shadow imaging tracking system can comprise at least a shadow-imaging sensor whereby a position of an LED is measurable by the shadow-imaging sensor. Thereby, a position in the two-dimensional space or in the three-dimensional space can be measured by the shadow-imaging sensor.

According to an embodiment, the shadow imaging tracking system comprises a tracker with three or more LEDs, wherein at least one of a 5D position or a 6D position of the tracker is tracked by measuring the shadow image on an optical sensor. The LEDs operate preferably in the infrared region.

According to an embodiment, the shadow imaging tracking system comprises a tracker for the reception of LED signals in a sequential manner or a plurality of trackers for the reception of a plurality of LED signals comprising a synchronization of each of the LED signals. The LED signals can be received in a blinking mode due to the fact, that the signal of only one LED signal is measurable at the same time. If the signals of more than one LED are to be received by a tracker or a plurality of trackers, a synchronization is required between the plurality of trackers. The synchronization may include the generation of synchronization signals. Advantageously the transmission of the synchronization signals is performed via wireless communication channels.

According to an embodiment, the shadow imaging tracking system comprises a shadow-imaging sensor for reception of at least two LEDs operating at different wavelengths, wherein the different wavelengths can be distinguishable by a filter or by a different sensitivity.

Any of the patient specific instruments, the instruments or the integrated measurement systems and/or the inertial measurement unit can be driven by an autonomous energy source such as a battery. At least one of the patient specific instruments, the instruments or integrated measurement systems can be connectable to a host computer. A display can be included with at least one of the instruments, the patient specific instruments or integrated measurement systems. At least one of the instruments, patient specific instruments or integrated measurement systems can communicate its tracking data to a host device whereby by at least one of the following elements: a data collecting element, a computation element, a display, a PC, a tablet, a mobile device. Alternatively or in addition thereto, one of the instruments, patient specific instruments or integrated measurement systems can communicate with at least one other instrument of the same or a different kind.

According to an embodiment, the instrument or the patient specific instrument comprises a memory for storing data, whereby the data can be one of patient data or imaging data. Such data are stored in the memory on a temporary or permanent basis to be used for the procedure.

According to an embodiment, the surgical instrument system comprises a memory for storing instrument data for the second instrument to be used together with the first instrument, whereby the instrument data can include at least one of an offset, a type of instrument or display data.

According to an embodiment, the instrument or at least one of the instruments or patient specific instruments comprises an instrument storage application software for execution on the instrument or the host computer. In particular, such instrument storage application software can include dedicated application software, which can be delivered with the instrument or patient specific instrument.

According to an embodiment, the tracking system or the inertial measurement unit is detachable from the patient specific instrument or instrument. The tracking system can be reusable for sterilization and clinic or refurbishment at the manufacturer's site.

According to an embodiment, the instrument or the patient specific instrument with the tracking system or the inertial measurement unit is of a single use type.

According to an embodiment, the patient specific instrument has a mating surface area, wherein a portion of the mating surface area is detachable from the instrument.

According to an embodiment, the tracking component is attachable by the defined mechanical coupling such that the relative position of the tracking system with respect to the instrument or the patient specific instrument and thereby with the anatomy is determined.

An advantage of the invention is to combine the advantages of patient matched devices and computer assisted surgery. It keeps the simplicity of patient matched devices to directly register the patient's anatomy and add the flexibility of computer assisted surgery to allow adjusting and fine-tuning the implant position during surgery, to ensure proper ligament balancing.

Total knee replacement (TKR) is one of the most widely performed orthopedic procedures worldwide. The two main important aspects of TKR are relating to achieving proper alignment of the prosthesis with respect to the mechanical axis of the leg and ensuring that ligaments are well balanced. In conventional surgery, they largely remain dependent on surgeon experience and subjective judgments of soft tissue balancing. Specifically, studies have shown that failure to align the components or unbalanced ligaments properly may lead to premature wear, propensity to dislocate and patient discomfort. Currently there are two technologies on the market to achieve an improved implant placement compared to conventional standard intervention: Computer assisted surgery systems (CAS) and patient specific instrumentation (PSI).

Computer assisted surgical systems (CAS) allow to measure or register the patient anatomy using markers attached to a patient's bone that are tracked by a stereo camera system. CAS technology is well established in the orthopedic market but only a limited percentage of total knee replacements (5-10%) are done using such systems. There are several reasons for this: Additional costs for the navigated procedures such as purchase cost of the system, per case costs for trackers/sterilization, increased OR time due to more complex workflow/registration of landmarks and additional incisions/pins to mount the trackers.

Patient specific instrumentation (PSI) or patient specific cut guides in total knee replacement is a new fast-growing trend that emerged in the last 5 years. Already up to 5-10% of all total knee replacements in the US and Europe are made using patient specific cut guides. To build a patient specific template the patient undergoes a CT or MRI scan from which accurate 3D models of the anatomical structures, in particular bones, are reconstructed. Based on these models a preoperative planning is done and customized guides are manufactured by 3D printing. Using these guides preoperative plan can be executed very efficiently, thus saving OR-time and limiting complexity. Drawback of patient specific cut guides are that additional time is required to check and approve the preoperative plan and there is no change to the plan possible during surgery. Individual adaptation of implant position to ensure proper balanced ligaments to ensure a stable and well functional knee joint is also not possible.

Patient specific instruments in combination with an integrated measurement system for surgical navigation surprisingly combine the best of both of these two technologies together as it keeps the simplicity of PSI to use a patient matched device to directly register the patient's anatomy and allow to adjust and fine-tune the implant position during surgery, like in CAS, to ensure proper ligament balancing. This can be achieved by miniaturizing and integrating the measurement technology directly into the patient specific instruments. The intended solution in this respect differentiates from any existing system on the market and combines the advantages of prior art approaches in a synergistic manner.

Surgeons already using patient specific instruments will benefit from having the possibility to change planning/cuts based on ligament balancing while keeping the simplicity of using cut blocks. CAS users will profit from a much quicker workflow in surgery, do not have to mount trackers with pin's and doing landmark acquisition. In other words, it keeps the simplicity to use a patient matched device and allows adjusting and fine-tuning the implant position during surgery to ensure proper ligament balancing, like in computer-assisted systems. In particular, the use of shadow imaging technology, which brings the necessary compactness required for the solution as computer assisted surgery use traditional imaging, i.e. a stereo camera, lens and passive or active target. The camera with the necessary lens results in large systems, like the ones proposed by AXIOS 3D® or Polaris by NDI™. Patient specific instruments lack today the possibility to adjust the cuts during the operation.

Shadow imaging typically uses a set of LEDs and an imager with a mask. By using four LEDs or more, the tracker can work with a single sensor instead of two for the traditional system. In addition, the use of a mask instead of a traditional optics results in a very compact system in particular for wide-angle systems. For example, a shadow imaging system with a 120-degree viewing angle can be made as compact as 2 to 3 mm thick. In addition, shadow imaging offers better precision, and better depth of focus.

Most advantageously, a surgical instrument system according to any of the preceding embodiments can be used for a navigation task to be performed in orthopedic treatments, such as knee or hip replacements, also in traumatic treatments or sports medicine. An alternative application of a surgical instrument system may include the measurement of a drilling or sawing position on a bone structure to place an implant precisely. Alternatively, the surgical instrument system according to any of the preceding embodiments may include kinematical measurements of a bone or bone structure relative to at least a second bone or bone structure. Alternatively the surgical instrument system can be used for any navigation task to be performed in the field of mandibular or dental surgery, e.g. for drilling operations or placement of dental implants.

A further possible application of a surgical instrument system according to any of the preceding embodiments includes treatments by arthroscopy. In particular, the position of the image generation unit relative to the anatomical structure or other instruments can be determined.

A surgical instrument system according to any of the preceding embodiments may be used also for spine treatment or for neurological treatments, in particular for determining the anatomical structure of the spine of the patient, as well as the placement of implants, such as screws or for navigation purposes during neurological treatments.

The use of a shadow imaging tracking system according to any of the preceding embodiments allows for obtaining a substantial reduction in size of the instruments as well as a further integration with other instruments. The size reduction comes together with a lightweight configuration of the components of the surgical instrument system. In any case, the shadow imaging tracking system can be coupled directly to the instrument or may form an integral part of the instrument. Furthermore, the assembly procedure on an anatomical structure, such as a bone is facilitated, mainly due to the obtainable reduction in size and weight. A shadow imaging tracking system in a surgical instrument system can be configured as a single-use application, as the sensors as well as the measurement and the result data can be generated and displayed by making use of a small-scale chip, which can be coupled to or integrated in the instrument.

A shadow imaging tracking system can further replace a conventional optical system, as optical lenses are no longer required. Therefore, a time-consuming calibration of the instruments can be dispensed with, as in particular no distortion effects have to be taken care of.

A shadow imaging tracking system can be operated by wireless data transmission technology, thus any cables obstructing the workspace can be dispensed with. Together with the possible integration of the tracking system into the instrument or patient specific instrument itself, the application of a shadow imaging tracking system allows for an unprecedented freedom and ease of movement for the medical personnel conducting the operation when making use of the instruments of a surgical instrument system configured according to any of the preceding embodiments.

Due to the fact, that the measurement is performed directly in the operation area forming the workspace, any human influence or any influence from other instruments present in the operation area is minimized. Conventional navigation systems suffer from the drawback that any camera placed outside the operation area has to be in a line of sight with the instruments handled inside the operation area. Therefore, medical personnel have to take care not to obstruct the line of sight of the camera at any time during operation procedure, which has the consequence that the freedom of movement for the medical personnel is substantially reduced.

The inertial measurement unit allows thus to determine the position of the patient, in particular also the position of the anatomical structure to be treated, in particular the bone structure. The inertial measurement unit can be integrated in the integrated measurement system. In particular, the inertial measurement unit can be integrated in to the optical source, in particular into any one of the LED's as previously described.

By making use of an inertial measurement unit the precision of the measurement results is increased due to sensor fusion effects, in particular in combination with the shadow imaging tracking system including an optical measurement. An inertial measurement unit is characterized by a high measurement frequency, whereas a considerably lower measurement frequency is obtainable by the optical measurement. Thus, the combination of these different measurement principles allows to increase measurement frequency on one hand and to allows to incorporate the discrete measurement results from optical measurements which are characterized by high precision into a combined result. The combination of different measurement principles thus allows to generate a feedback for any interpolation between the discrete measuring points resulting from the optical measurements of the tracking system from a different measurement approach, the position measurement by the inertial measurement system. If the results of high frequency measurement results from the inertial measurement unit match with the interpolated curve generated from the discrete optical measurements, such a correlation provides an independent feedback control. In particular, deviations from the correlations observed or calculated from the observed data may indicate an error, for instance a malfunction of the surgical instrument system or and damage thereof. For this reason, any combination of measurement principles in an integrated measurement system surprisingly results in an unexpected gain in reliability of the entire surgical instrument system.

Independently of these previously discussed possible synergies resulting in a higher precision and a higher reliability of the surgical instrument system, an inertial measurement unit may provide results for performing kinematic analyses. An acceleration sensor attached to an anatomic structure, such as a bone may provide results to determine axes for movements or rotational centers for such movements which are to be performed by the anatomic structure.

BRIEF DESCRIPTION OF THE DRAWINGS

The invention will be explained in more detail in the following with reference to the drawings. There are shown in a schematic representation in.

DETAILED DESCRIPTION

Figure 1:
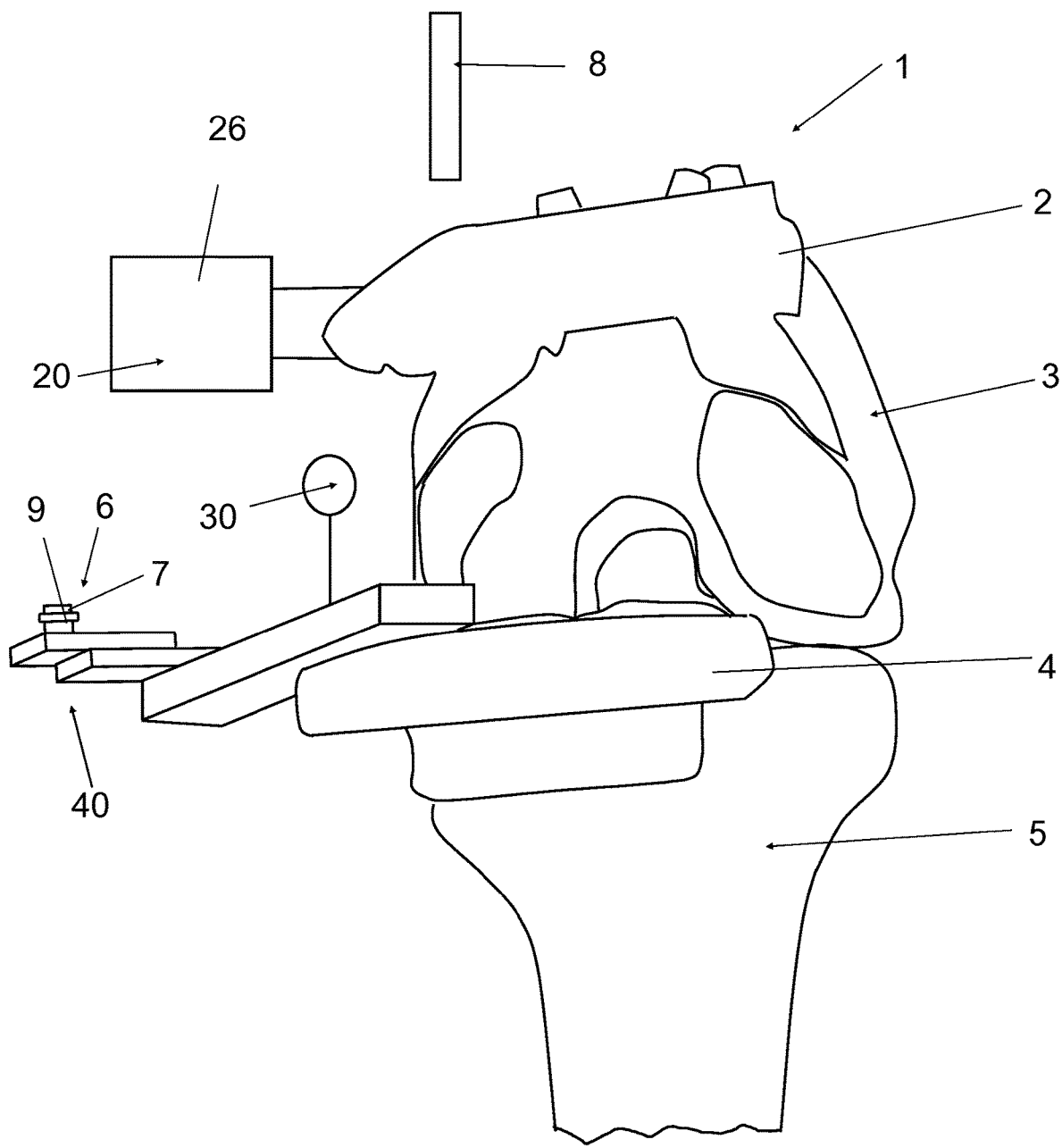
FIG. 1 a surgical instrument system with integrated measurement system and instrument tracked relative to the measurement system according to a first embodiment of the invention, FIG. 2 a surgical instrument system with integrated measurement system for a patient specific instrument and an instrument according to a second embodiment of the invention, FIG. 3 a surgical instrument system with integrated measurement system for a first patient specific instrument, a second patient specific instrument and an instrument according to a third embodiment of the invention.

FIG. 1 shows an embodiment of the surgical instrument system 1 comprising a patient specific instrument 2, 4 attached to an anatomical structure 3, 5 and an instrument 8 for performing a surgery on the anatomical structure. As an example, the anatomical structure for a knee replacement treatment is shown in FIG. 1. The first anatomical structure 3 comprises a portion of the femur. The second anatomical structure 5 comprises a portion of the tibia. The first patient specific instrument 2 is configured as a template attached to the femur. The second patient specific instrument 4 is configured as a template attached to the tibia. The first patient specific instrument 2 comprises an integrated measurement system 20. The integrated measurement system 20 can comprise a patient specific instrument sensor 26. The patient specific instrument sensor 26 can receive information from a tracking system (not shown). By means of the tracking system 20, the spatial position of the patient specific instrument sensor 26 is determinable. Furthermore, the second patient specific instrument 4 can be disposed with an integrated measurement system 40. The integrated measurement system 40 can be configured in the same way as the integrated measurement system 20 of the patient specific instrument 2, a configuration, which is not shown in FIG. 1. Alternatively or in addition thereto, the integrated measurement system 40 can include a tracking system 6, including a tracker element 7 comprising a signal emitter 9, which is configured to send a signal to the patient specific instrument sensor 26. The integrated measurement system 20 transforms the signal from the signal emitter 9 into a relative patient specific instrument position information. In addition, the integrated measurement system comprises an inertial measurement unit 30 configured to determine the position of the patient.

Figure 2:
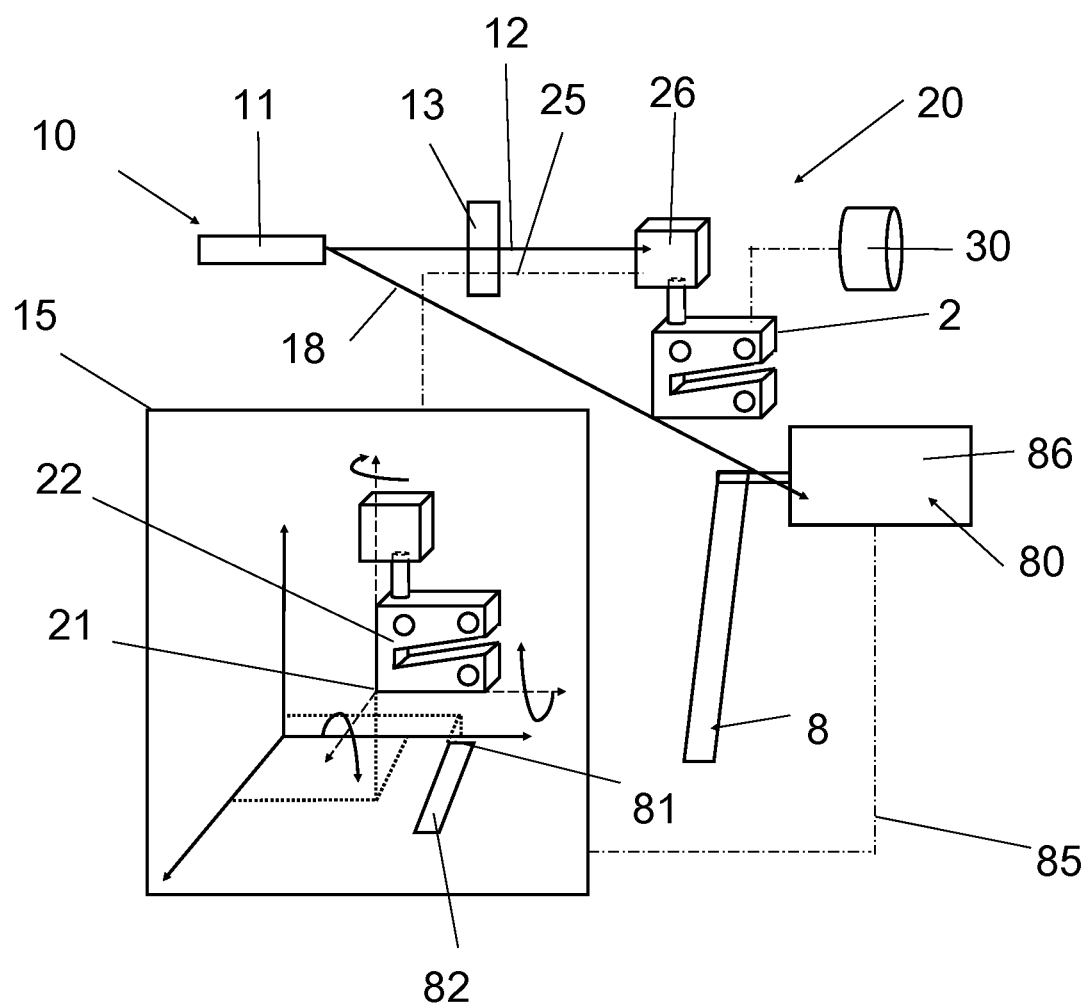

According to the configuration of the surgical instrument system 1 shown in FIG. 2, an initial position of the patient specific instrument 2 is registerable by a patient specific instrument sensor 26, such that a patient specific instrument position information is obtainable. A source 10, comprising a tracking signal emitter 11 is placed remotely from the patient specific instrument. The tracking signal emitter 11 can emit a tracking signal 12, which is received by the patient specific instrument sensor 26. The position of the source 10 and for this reason, the tracking signal emitter 11 is known. The patient specific instrument sensor 26 determines upon receipt of the tracking signal 12 its position in relation to the tracking signal emitter 11. Thereby the position of the patient specific instrument sensor 26 in a three-dimensional coordinate system such as a Cartesian coordinate system can be determined. The origin of this coordinate system can be placed at the location of the source 10 or any location in a predetermined distance from the source or the tracking signal emitter. The source 10 can in particular be a light source. The patient specific instrument sensor 26 can comprise an imaging device. Such an imaging device can be composed of a plurality of sensitive pixels. In particular, these pixels can be sensitive to the receipt of light from the light source. Between the light source and the imaging device, a shadow-generating device 13 is arranged. Such a shadow-generating device can be a grid, a grating or an array, in particular a micro lens array. The shadow-generating device casts a shadow on the imaging device if light from the light source is projected onto the shadow-generating device. The imaging device can record the image of the shadow. Due to the fact, that the position of the shadow-generating device with respect to the imaging device is known, the shadow creates a shadow on the imaging device from which the position of the light source can be determined. In case the patient specific instrument sensor 26 is configured as a two-dimensional sensor, the elevation of the light source can be computed from the pattern the shadow casts on the surface of the imaging device. By repeating this measurement in a plurality of distinct locations of the patient specific instrument sensor, a plurality of elevation values is obtained. By application of triangulation rules, the position of the light source can be determined. In turn, the position of the patient specific instrument sensor and accordingly the position of the patient specific instrument 2 is determined based on the location of the light source.

The precision of the positioning can be enhanced if the shadow generating device creates a plurality of shadows on the imaging device, as outlined for instance in WO2012/007561A2.

In addition, the integrated measurement system comprises an inertial measurement unit 30 configured to determine the position of the patient. An inertial measurement unit is characterized by a high measurement frequency, whereas a considerably lower measurement frequency is obtainable the optical measurement. Thus, the combination of these different measurement principles allows to increase measurement frequency on one hand and to allows to incorporate the discrete measurement results from optical measurements which are characterized by high precision into a combined result. Moreover, an acceleration sensor attached to an anatomic structure, such as a bone, may be used for a kinetic analysis. Such a kinetic analysis may in turn provide results to determine axes for movements or rotational centers for such movements which are to be performed by the anatomic structure.

As an example, an inertial measurement unit 30 can be attached to the distal femur bone for a knee replacement. The inertial measurement unit can comprise an acceleration sensor. The acceleration sensor can be used to perform a kinetic analysis. The kinetic analysis of the movement of the femur bone can determine the center of rotation of the hip joint. Along therewith, an axis of rotation can be generated or calculated, which can be used by the optical system to navigate the knee joint or the respective sections of the anatomic structure.

The patient specific instrument sensor 26 thus provides the position data to an integrated measurement system 20 for creating a patient specific instrument position information 25. This patient specific instrument position information 25 is transformable into a patient specific instrument coordinate position information 21 in a three-dimensional coordinate system by a computer. The computer can be part of the integrated measurement system 20 or the integrated measurement system can transmit the data to a remote computer. The computer can contain a model 22 of the patient specific instrument 2 such that the position of the patient specific instrument can be shown on a display 15. Furthermore, the computer can contain a model of the anatomic structure of the patient. Thereby the position of the patient specific instrument with respect to the anatomic structure can be displayed in a virtual model.

The virtual model can be viewed, rotated, enlarged or cut open to show sections thereof, whereby the exact location and process of the treatment can be shown, planned and monitored. The model of the anatomic structure can have been generated by e.g. by radiography or MRI data.

The patient specific instrument 2 may have been generated by a stereolithographic or an additive manufacturing method. The model 22 for the patient specific instrument 2 is matched with the model of the patient's anatomic structure so to provide a virtual three-dimensional model of the location of the patient specific instrument in its position on the patient's anatomic structure. Therefore, the model can reflect the position of the patient specific instrument with high accuracy.

Moreover, an initial position information of the instrument 8 is obtainable by an integrated measurement system 80, which is attached to the instrument 8. The integrated measurement system 80 can be of the same configuration as the integrated measurement system 20. The integrated measurement system 80 can comprise an instrument sensor 86. An initial position of the instrument 8 is registerable by the instrument sensor 86, such that an instrument position information 85 is obtainable. The source 10 comprising the tracking signal emitter 11 is placed remotely from the instrument 8. The tracking signal emitter 11 can emit a tracking signal 18, which is received by the instrument sensor 86. The position of the tracking signal emitter 11 is known. The patient specific instrument sensor 86 determines upon receipt of the tracking signal 18 its position in relation to the tracking signal emitter 11. Thereby the position of the instrument sensor 86 in a three-dimensional coordinate system, such as a Cartesian coordinate system can be determined. The instrument position information 85 is transformable into an instrument position coordinate information 81 in a three-dimensional coordinate system by the computer. The instrument coordinate position information 81 is matched with the patient specific instrument coordinate position information 21, to locate a model 82 of the instrument 8 in the coordinate system. Thereby the position of the instrument relative to the position of the patient specific instrument is determined. The results obtained from the position sensor or acceleration sensors of the inertial measurement unit 30 can be added to the instrument position information 85 or the instrument position coordinate information 81. the precision of the measurement results is increased due to sensor fusion effects, in particular in combination with the shadow imaging tracking system including an optical measurement. An inertial measurement unit 30 making use of position or acceleration sensors is characterized by a high measurement frequency, whereas a considerably lower measurement frequency is obtainable by the optical measurement. Thus, the combination of these different measurement principles allows to increase measurement frequency on one hand and to allows to incorporate the discrete measurement results from optical measurements which are characterized by high precision into a combined result. The combination of different measurement principles thus allows to generate a feedback for any interpolation between the discrete measuring points resulting from the optical measurements of the tracking system and the position measurement results obtained by the inertial measurement system.

Figure 3:
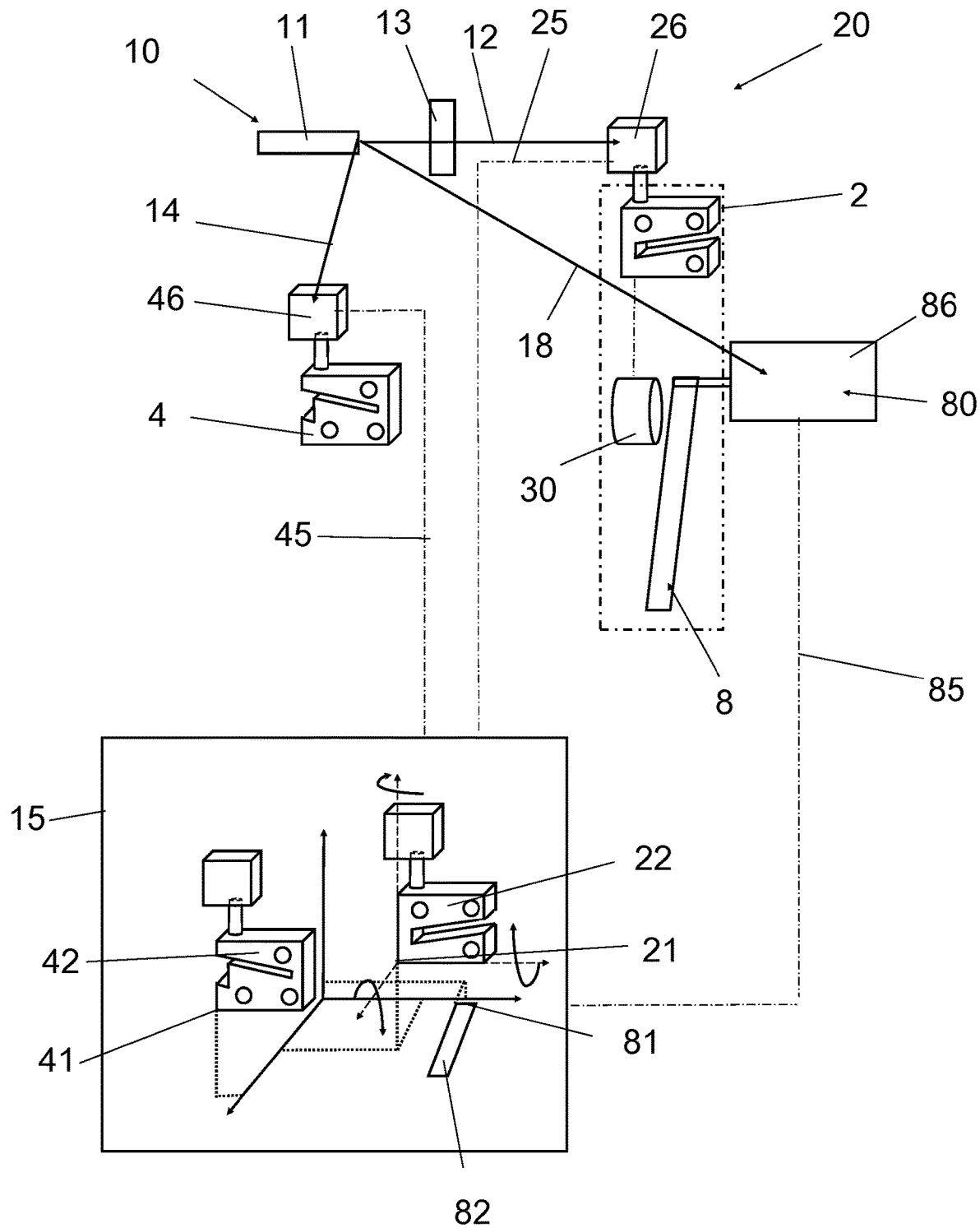

FIG. 3 shows a third embodiment including a first anatomical structure 2 and a second anatomical structure 4. The embodiment according to FIG. 3 differs from the previous embodiments in that the first and second patient specific instruments 2, 4 are each equipped with an integrated measurement system 20, 40. For the description of the first patient specific instrument and its integrated measurement 20 it is referred to FIG. 2.

In FIG. 3 a schematic box shape is shown grouping the instrument 8, the patient specific instrument 2 and the inertial measurement unit 30, configured as the acceleration sensor, so that they are formed as a single unit.

An initial position of the second patient specific instrument 4 is registerable by a patient specific instrument sensor 46, such that a patient specific instrument position information is obtainable. A source 10, comprising a tracking signal emitter 11 is placed remotely from the patient specific instrument. The tracking signal emitter 11 can emit a tracking signal 12, which is received by the patient specific instrument sensor 46. The position of the source 10 and the tracking signal emitter 11 is known. The patient specific instrument sensor 46 determines upon receipt of the tracking signal 12 its position in relation to the tracking signal emitter 11. Thereby the position of the patient specific instrument 4 in a three-dimensional coordinate system such as a Cartesian coordinate system can be determined. The origin of this coordinate system can be placed at the location of the source 10 or any location in a predetermined distance from the source or the tracking signal emitter. In particular, the coordinate system is the same as used for the first patient specific instrument 2 and the instrument 8.

The patient specific instrument sensor 46 thus provides the position data to an integrated measurement system 40 for creating a patient specific instrument position information 45. This patient specific instrument position information 45 is transformable into a patient specific instrument coordinate position information 41 in a three-dimensional coordinate system by a computer. The computer can be part of the integrated measurement system 40 or the integrated measurement system can transmit the data to a remote computer. The computer can contain a model 42 of the patient specific instrument 4 such that the position of the patient specific instrument can be shown on a display 15. Furthermore, the computer can contain a model of the anatomic structure 5 of the patient, as shown in FIG. 1. Thereby the position of the patient specific instrument with respect to the anatomic structure can be displayed in a virtual model.

In an alternative embodiment, any of the integrated measurement systems 20, 40, 80 can be replaced or supplemented by a signal emitter such as the signal emitter 9 shown in FIG. 1.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of an element or compound selected from the group consisting of A, B, C . . . and N, the text should be interpreted as requiring only one element from the group, not A plus N, or B plus N, etc.

The invention claimed is:

1. A surgical instrument system for treatment of an anatomical structure comprising at least one of an instrument or a patient specific instrument for performing the treatment of the anatomical structure, wherein the at least one instrument or the patient specific instrument comprises an integrated measurement system coupled to the at least one instrument or the patient specific instrument for tracking the at least one instrument or the patient specific instrument relative to the anatomical structure via a tracking system, wherein the tracking system is housed within the integrated measurement system, wherein the tracking system comprises a shadow imaging tracking system comprising an optical source, a shadow-generating device and a patient specific instrument sensor, whereby an initial position of the instrument or the patient specific instrument is registerable by the patient specific instrument sensor, whereby the shadow-generating device is arranged between the optical source and an imaging device for generating a shadow, whereby the shadow imaging tracking system is configured to compute an elevation of the optical source from a pattern the shadow casts on a surface of the imaging device and the integrated measurement system comprises an inertial measurement unit coupled to the at least one instrument or the patient specific instrument, configured to determine at least one of a position of a patient or an acceleration or rotation of a body part of the patient, and configured to perform a kinetic analysis of the anatomical structure and wherein the shadow imaging tracking system is integrated in the at least one instrument or the patient specific instrument.

2. The surgical instrument system of claim 1, wherein the tracking system includes a single tracker element for allowing redundant measurements.

3. The surgical instrument system of claim 1, wherein the tracking system is used for tracking at least one of the patient specific instrument or the instrument relative to the anatomical structure, whereby the tracking system allows at least one combination of relative measurement between the patient specific instrument and the instrument or wherein the tracking system is attached to a plurality of patient specific instruments or instruments.

4. The surgical instrument system of claim 1, wherein the shadow imaging tracking system comprises at least a shadow-imaging sensor, whereby a position of a light emitting diode (LED) is configured to be measured by the shadow-imaging sensor or wherein the shadow imaging tracking system comprises a tracker with three or more LEDs, wherein at least one of a five degrees of freedom (5D) position or a six degrees of freedom (6D) position of the tracker can be tracked by measuring a shadow image on an optical sensor or a tracker for the reception of LED signals in a sequential manner or wherein a plurality of trackers for the reception of a plurality of LED signals is provided, comprising a synchronization of each of the LED signals.

5. The surgical instrument system of claim 1, wherein the shadow imaging tracking system comprises a shadow imaging sensor for reception of at least two light emitting diodes (LEDs) operating at different wavelengths, wherein the different wavelengths are distinguishable by a filter or by different ranges of differing sensitivity.

6. The surgical instrument system of claim 1, wherein the integrated measurement system comprises the inertial measurement unit and an optical measurement.

7. The surgical instrument system of claim 1, wherein the patient specific instrument is configured to perform a position measurement of at least one of a first anatomical structure and a second anatomical structure or to combine it with the measurement of the patient's position as obtained from the inertial measurement unit.

8. The surgical instrument system of claim 7, wherein the first anatomical structure is disposed with a first patient specific instrument and the second anatomical structure is disposed with a second patient specific instrument.

9. The surgical instrument system of claim 8, wherein the second patient specific instrument is configured to be fixed to the second anatomical structure and comprises the integrated measurement system to track the position of the second anatomical structure relative to the first anatomical structure.

10. The surgical instrument system of claim 1, wherein the tracking system or the inertial measurement unit is detachable from the patient specific instrument to be reusable for sterilization and clinic or refurbishment at a manufacturer's site or wherein the patient specific instrument with the tracking system or the inertial measurement unit is of a single use type.

11. The surgical instrument system of claim 1, wherein the tracking system or the inertial measurement unit is attachable by a defined mechanical coupling such that a relative position of the tracking system or the inertial measurement unit with respect to the patient specific instrument and thereby with respect to the anatomy is determined.

12. The surgical instrument system of claim 1, whereby the patient specific instrument and the instrument and the inertial measurement unit are formed as a single unit.

13. The surgical instrument system of claim 1, wherein at least one of a position or a rotation of the instrument relative to the patient specific instrument is adjusted such that an adjustment can be restricted to a single or multiple movement, wherein the movement can be one of a linear movement or a rotational movement or the movement is restricted by a mechanical interface.

14. The surgical instrument system of claim 1, wherein at least one of the patient specific instrument or the instrument or the integrated measurement system or the inertial measurement unit is driven by an autonomous energy source comprising a battery.

15. The surgical instrument system of claim 1, wherein at least one of the patient specific instrument or the instrument or the integrated measurement system or the inertial measurement unit is configured to connect to a host computer comprising a display.

16. The surgical instrument system of claim 1, wherein at least one of the patient specific instrument or the instrument or the integrated measurement system or the inertial measurement unit is configured to communicate with at least one other instrument of the same or a different kind or wherein at least one of the instrument or the patient specific instrument communicates its tracking data to a host device by at least one of the following elements: a data collecting element, a computation element, a display, a PC, a tablet, or a mobile device.

17. The surgical instrument system of claim 1, wherein at least one of the instrument or the patient specific instrument comprises a memory for storing data, comprising patient data or imaging data to be used for a procedure.

18. The surgical instrument system of claim 1, wherein a first and a second instrument are provided, wherein the first instrument comprises a memory for storing instrument data for the second instrument to be used together with the first instrument, wherein the instrument data can include at least one of an offset, a type of instrument or display data.

19. The surgical instrument system of claim 1, wherein at least one of the instrument or the patient specific instrument comprises an instrument storage application software for execution on the instrument or patient specific instrument or on the host computer.

20. The surgical instrument system of claim 1, wherein at least one of the patient specific instruments has a mating surface area, wherein a portion of the mating surface area can be detachable from the patient specific instrument.

* * * * *